United States Patent
Perry

(10) Patent No.: US 9,572,685 B2
(45) Date of Patent: Feb. 21, 2017

(54) INSTRUMENT FOR IMPLANTING IMPLANT DEVICE

(71) Applicant: Alphatec Spine, Inc., Carlsbad, CA (US)

(72) Inventor: Thomas Perry, Oceanside, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 0 days.

(21) Appl. No.: 14/663,508

(22) Filed: Mar. 20, 2015

(65) Prior Publication Data

US 2015/0265321 A1 Sep. 24, 2015

Related U.S. Application Data

(60) Provisional application No. 61/955,947, filed on Mar. 20, 2014.

(51) Int. Cl.
| | |
|---|---|
| *A61F 2/46* | (2006.01) |
| *A61F 2/44* | (2006.01) |
| *A61B 17/80* | (2006.01) |
| *A61F 2/30* | (2006.01) |

(52) U.S. Cl.
CPC .......... *A61F 2/4611* (2013.01); *A61F 2/447* (2013.01); *A61F 2/4455* (2013.01); *A61B 17/808* (2013.01); *A61F 2002/30176* (2013.01); *A61F 2002/30579* (2013.01); *A61F 2002/30604* (2013.01); *A61F 2002/30797* (2013.01); *A61F 2002/30808* (2013.01); *A61F 2002/30904* (2013.01); *A61F 2002/4627* (2013.01); *A61F 2310/00017* (2013.01); *A61F 2310/00023* (2013.01)

(58) Field of Classification Search
CPC ..................................... A61F 2/4611
See application file for complete search history.

(56) References Cited

U.S. PATENT DOCUMENTS

| | | | |
|---|---|---|---|
| 6,174,311 B1 * | 1/2001 | Branch | A61B 17/1671 606/60 |
| 6,447,546 B1 | 9/2002 | Bramlet et al. | |
| 7,594,919 B2 * | 9/2009 | Peterman | A61F 2/4425 606/99 |
| 8,460,388 B2 | 6/2013 | Kirwan et al. | |
| 2010/0160984 A1 * | 6/2010 | Berry | A61F 2/447 606/86 A |
| 2010/0185289 A1 | 7/2010 | Kirwan et al. | |
| 2011/0196494 A1 * | 8/2011 | Yedlicka | A61F 2/4455 623/17.16 |
| 2011/0270257 A1 * | 11/2011 | Moore | A61F 2/44 606/90 |

(Continued)

OTHER PUBLICATIONS

Intelligent Technology Simplified Surgery, Pegasus Surgical Technique Guide, 21 pages, LIT-84456B, Jul. 5, 2013.

*Primary Examiner* — Nicholas Plionis
(74) *Attorney, Agent, or Firm* — Dinsmore & Shohl LLP

(57) ABSTRACT

An instrument for attachment to and insertion of an implant device is provided. The instrument has a handle and a pair of retaining posts extending longitudinally from a distal end of the handle. Each of the pair of retaining posts have an end dimensioned to engaged a respective threaded bore of the implant device. Also, a post drive mounted to the handle and mechanically connected to each of the retaining posts so as to engage the retaining posts simultaneously is provided.

17 Claims, 4 Drawing Sheets

(56) References Cited

U.S. PATENT DOCUMENTS

2012/0046751 A1* 2/2012 Muhanna ............ A61F 2/4455
                                                            623/17.16
2013/0150968 A1   6/2013 Dinville et al.
2013/0226300 A1   8/2013 Chataigner et al.

* cited by examiner

INSTRUMENT FOR IMPLANTING IMPLANT DEVICE

RELATED APPLICATION

This application claims priority of U.S. Provisional Application No. 61/955,947 filed Mar. 20, 2014, the contents of which are incorporated herein by reference.

FIELD OF THE INVENTION

The present invention is related to an instrument for implanting a medical device and in particular to an instrument for implanting a medical device between two spinal vertebrae.

BACKGROUND OF THE INVENTION

Instruments used for implanting implant devices are currently known and used. Implant devices having an anchor so as to fix the implant device within the body are also known. Such implant devices further include an anchoring device. Such implant devices are fixed to the instrument so as to stabilize the implant device during operation. Thus, the implant device may include a pair of threaded bores configured to receive a pair of threaded posts.

Current instruments for implanting implant devices are configured to both retain the implant device and also actuate the anchor such that once the implant device is inserted within the body the anchor may be deployed and the implant device fixed in a determined position within the body. Accordingly, the implant device must be mounted to the instrument. Subsequent to implanting the implant device, the threaded posts are withdrawn from the corresponding threaded bores.

Currently such instrument devices have a separate actuator for each of the retaining posts. Thus, the time required to mount the implant device to the instrument is dependent upon the time it takes to individually couple each of the threaded posts to the respective bores. Also, operation time is based upon not only the time it takes to deploy the anchor but also the time required to withdraw each of the threaded posts from the respective threaded bores. Further, current devices have visual indicia which provide a reference to the depth at which the implant device should be implanted. In certain areas of the body the depth of implantation is critical to the optimal functioning of the implant device.

Accordingly, it remains desirable to have an instrument for attaching and implanting an implant device wherein the installation time of the implant device and the operation time of the procedure is reduced relative to the current art, and the depth at which the implant device is implanted is known.

SUMMARY OF THE INVENTION

An instrument for implanting an implant device is provided. The implant device includes an anchor and an actuator configured to deploy the anchor. The anchor is deployable so as to fix the implant device within the body. The implant device further includes a pair of threaded bores. The threaded bores are configured to receive a pair of retaining posts of said instrument so as to fix the implant device with respect to the instrument and stabilize the implant device during the deployment of the anchor.

The instrument includes a handle. The handle is dimensioned to be gripped by a user. The instrument further includes a pair of retaining posts. Each of the retaining posts extends longitudinally from a distal end of the handle and is generally parallel to each other. Each of the pair of retaining posts has a threaded end dimensioned to engage a respective threaded bore of the implant device.

The instrument further includes a post drive. The post drive is mounted to the handle. The post drive is mechanically connected to each of the pair of retaining posts. The post drive is further configured to engage the pair of retaining posts simultaneously. Thus, when both threaded ends are registered to a respective threaded bore the post drive may drive and engage both retaining posts simultaneously within the threaded bores and thereby reduce installation time with respect to the current art. It is should also be appreciated that upon successful implantation of the implant device, the post drive may be actuated so as to disengage both of the pair of retaining posts from the threaded bores simultaneously, thus reducing operation time and making the operation less invasive respective to the current art.

The instrument may further include a stop. The stop is disposed adjacent the distal end of the instrument. The stop is configured to physically prevent the implant device from being inserted into a body past a predetermined depth.

In one embodiment of the stop, the stop is a tubular member having a distal end with a planar surface. The stop includes a stop drive. The stop drive is configured to axially displace the distal end so as to adjust the maximum depth of the implant within the body. The planar surface is generally orthogonal to the outer surface of the housing and provides a contact surface for physically preventing further insertion of the implant device within the body.

BRIEF DESCRIPTION OF THE DRAWINGS

A better understanding of the present invention will be had upon reference to the following detailed description when read in conjunction with the accompanying drawings wherein like reference characters refer to like parts throughout the several views and in which.

DETAILED DESCRIPTION OF THE INVENTION

An instrument for implanting an implant device into a patient is provided. The instrument has a handle that can be grasped by a user, e.g. a surgeon, and two retaining posts that engage and securely attach the implant device to the instrument via two threaded bores in the implant device. The instrument also has a post drive that is in mechanical communication with and configured to simultaneously rotate the two retaining posts. In this manner the user can simultaneously engage both retaining posts with the implant device.

With reference now to FIGS. 1-4, an illustrative example of an embodiment of an instrument 10 for implanting an implant device 400 (shown in FIGS. 5 and 6) is shown. The instrument 10 may be configured for use with the implant device 400. The instrument 10 includes a handle 12. The handle 12 is dimensioned to be gripped by a user.

Figure 6:
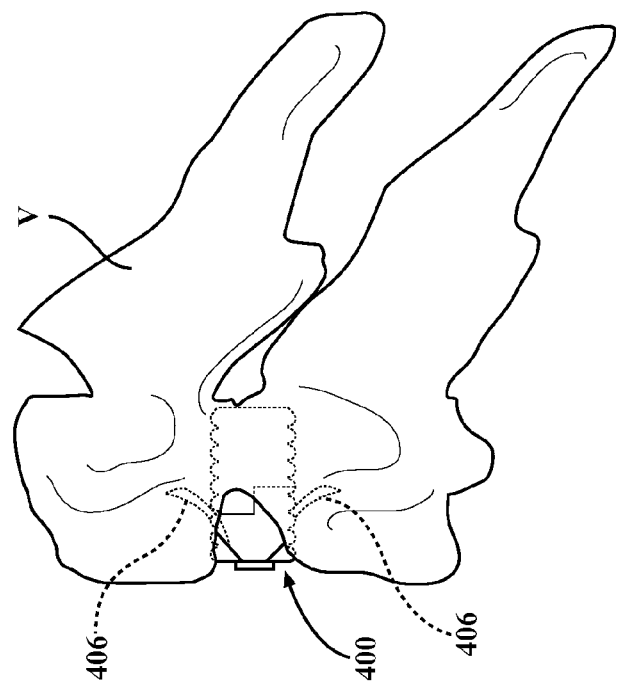
FIG. 6 is a side view of the implant device shown in FIG. 5 implanted into a pair of adjacent vertebrae bone.
Figure 5:
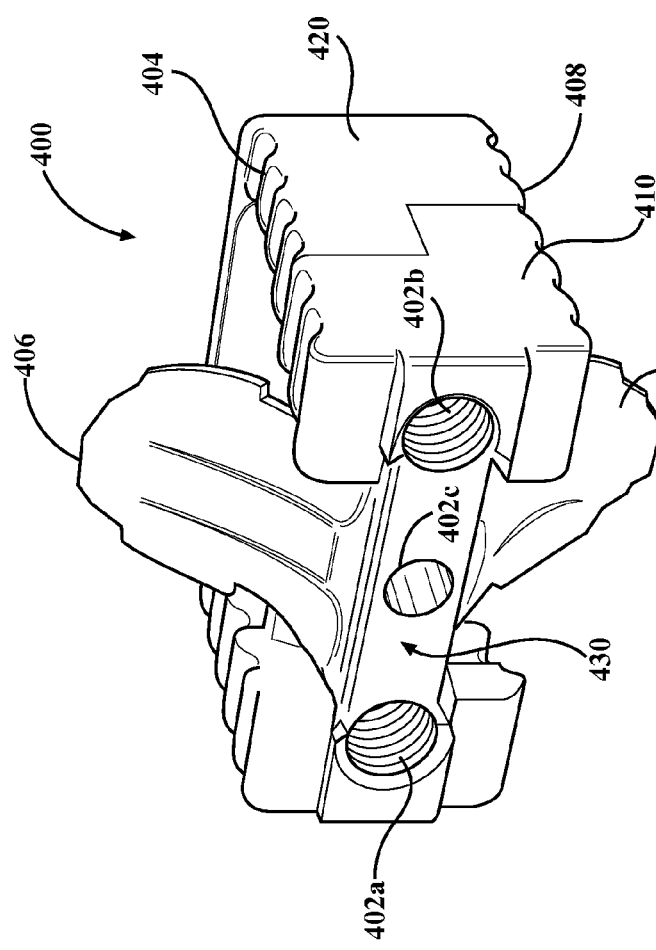
FIG. 5 is a perspective view of an implant device that can be implanted by the instrument shown in FIG. 1.

With reference now to FIGS. 5 and 6, the implant device 400 configured for use with the instrument 10 is shown. The implant device 400 includes an anterior portion 410 and a posterior portion 420, collectively referenced herein as a "Cage." The anterior portion 410 and posterior portion 420 are coupled together and enclose a space configured to hold a biomaterial such as a bone graft. The implant device 400 further includes an anchor 430. The anchor 430 is configured to engage the anterior portion 410 such that anchor members 406 of the anchor 430 may be driven over opposite sides of the anterior portion 410 and anchor the device 400 to the vertebrae V as shown in FIG. 6.

The anterior portion 410 includes a pair of threaded bores 402a, 402b on opposite sides of the anterior portion 410. The anchor 430 includes a third bore 402c that is disposed in between the peripheral bores 402a and 402b. The third bore 402c may be threaded. Third bore 402c provides access to an actuator of the instrument 10 (not shown) to deploy the pair of anchor members 406 of the anchor 430. The actuator drives the anchor members 406 outwardly with respect to a top surface 404 and bottom surface 408 of the implant device 400 so as to fix the implant device 400 within the vertebrae V.

Looking back to FIGS. 1-4, the instrument 10 may include a housing 14. The housing 14 may be formed of a polyetheretherketone, titanium, stainless steel, or any other material having sufficient structural rigidity to support implantation of the implant device 400 and which is also approved for medical use. The housing 14 has a longitudinal axis 15 and extends longitudinally away from a distal end 16 of the handle 12. The housing 14 may be a tubular structure having a generally rectangular cross section.

The housing 14 may include a first body portion 18 and a second body portion 20. The second body portion 20 includes a neck 22 and an outer housing 24. The neck 22 is angled so as to narrow as the neck 22 extends from a distal end of the first body portion 18 to a proximal end of the outer housing 24. The second body portion 20 includes three bores 20a, 20b, 20c (FIGS. 3 and 4) which are registered to align with the bores 402a, 402b and 402c of the implant device 400 when the implant device is installed to the instrument 10.

It is appreciated that terms proximal and distal are applied herein to denote specific ends of components of the instrument described herein. A proximal end refers to the end of an instrument nearer to an operator of the instrument when the instrument is being used. A distal end refers to the end of a component further from the operator and extending towards a surgical area of a patient and/or the implant.

The first body portion 18 includes a body member 26 having a pair of side walls 26a, 26b, a top wall 26c and a bottom wall (not shown). The body member 26 includes a body cavity 28 and a collar 30 disposed on a proximal end of the body member 26. The collar 30 includes a solid support portion having three bores 30a, 30b, 30c. The bores 30a, 30b, 30c are coaxial with bores 20a, 20b, 20c.

The instrument includes a pair of retaining posts 34. The retaining posts are shown as a generally elongated cylindrical member, and are rotatably disposed within the housing 14. A proximal end of the retaining posts 34 is rotatably held within bores 30a, 30b of the collar 30 of the housing 14. The distal ends of the retaining posts are rotatably disposed within bores 20a and 20b of the outer housing 24. The retaining posts 34 each include a threaded end 36 configured to engage bores 402a and 402b of the implant device 400. It should be appreciated by those skilled in the art that ends 36 are shown as being threaded for illustrative purposes only and the ends 36 may be smooth, as may be bores 402a and 402b.

The retaining posts 34 may be translated axially with respect to the housing 14 as well as rotated within the bores 30a, 30b and bores 20a, 20b. A post drive 38 is provided to rotatably displace the retaining posts 34. Specifically, the post drive 38 is configured to simultaneously rotate the retaining posts 34. An illustrative example of the post drive 38 is provided in FIGS. 2-4. The post drive 38 may include an outer gear 40 and a pair of planetary gears 42. The post drive 38 with outer gear 40 may be formed as part of the handle 12, or may be a separate piece fixed to the handle 12. For example, the post drive 38 can be part of the handle 12 or first body portion 18 and be operable to rotate freely from or with respect to handle 12 or first body portion 18.

Each of the planetary gears 42 meshes with the outer gear 40. The outer gear 40 includes a plurality of teeth 41 encircling an inner circumferential surface of the outer gear 40. Each of the planetary gears 42 include a plurality of teeth 43 bounding an outer circumferential surface of the planetary gear 42, wherein rotation of the outer gear 40 rotates the planetary gears 42. Each of the planetary gears 42 is fixed to a respective retaining post 34, so as to rotate the respective retaining post 34 when the outer gear 40 is rotated.

The handle 12 may further include an annular flange 44 extending inwardly and in contact with a proximal end face 41 of the outer gear 40. A pair of biasing members 46, e.g. coil springs, are mounted to a proximal end 35 of the retaining posts 34 and disposed between the annular flange 44 and each of the respective planetary gears 42. The biasing members 46 are configured to urge the planetary gears 42 and attached retaining posts 34 in a direction away from the annular flange 44 so as to expose the threaded ends 36 beyond the distal end of the housing 14. The biasing members 46 may ease or facilitate the initial coupling of instrument 10 to the implant device 400 by allowing alignment of the threaded ends 36 of the posts 34 to individually engage each bore 402a and 402b of the device 400.

In operation, the biasing members 46 urge the threaded ends 36 of the retaining posts 34 beyond the distal end of the housing 14. Rotation of the outer gear 40 relative to the handle 12 rotates each retaining post 34 simultaneously. When the threaded ends 36 are registered with a respective threaded bore 402a and 402b of the implant device 400, the rotation of the threaded ends 36 engages bores 402a and 402b of the implant device 400, so as to pull the implant device 400 into contact with the distal end of the outer housing 24. In this manner, the implant device 400 is securely attached to the instrument 10.

The handle 12 may include a pair of threaded openings 48 opposite of each other. The openings 48 may be configured to hold a stem 50 (FIG. 3) that may be coupled with one or more additional handles (not shown) to provide a counter torque during coupling of the device 400 and/or deployment of the anchor 406 as described here. Accordingly, the user may be able to insert the stem 50 of an additional handle within a desired opening 48 so as to assist in holding the handle 12 steady while rotation of the outer gear 40 about the planetary gears 42 is executed. Additionally, the additional handle may assist in holding the handle 12 steady during rotation of a T-handle or other drive handle coupled to an anchor drive mechanism as described below.

The handle 12 is generally cylindrical and includes a threaded bore 53 configured to house an anchor drive 54 with a threaded outer surface. The threaded bore 53 is generally coaxial with the body cavity 28 of the housing 14. The threaded bore 53 includes an inner wall which is threaded. The inner wall may include, for example, an Acme thread or another threaded profile suitable for drive systems including but not limited to a worm gear thread, an Acme thread, and the like. The proximal end of the anchor drive 54 includes a receiving portion 56 configured to receive a stem of an auxiliary handle (not shown). The auxiliary handle is configured to be inserted into the receiving portion 56 of the anchor drive 54 within the handle 12 as described below.

The anchor drive 54 may be in mechanical contact with an elongated shaft 58 extending longitudinally through the body cavity 28 of the housing 14 and the cavity 52 of the handle 12. A distal end 60 of the elongated shaft 58 may or may not be threaded and engages the bore 402*c* of the implant device 400. The elongated shaft 58 may have a generally cylindrical shape. A proximal end of the elongated shaft 58 has a flanged portion 63 that is in mechanical contact with a distal end of the anchor drive 54. The anchor drive 54 is inserted and threadingly engaged with the threaded bore 53 of the handle 12. The proximal end of the anchor drive 54 includes the receiving portion 56 configured to receive in a tight fit manner a stem of an auxiliary handle (not shown). The auxiliary handle is configured to turn the anchor drive 54 which engages a proximal end of the elongated shaft 58 and/or the flanged portion 63 so as to axially displace the elongated shaft 58.

The flanged portion 63 engages the distal end of the anchor drive 54. The shaft 58 may rotate freely relative to the anchor drive 54 as the flanged portion 63 rotates within the recess of the distal end thereof. The shaft 58 may be rotated by an anchor coupler 61 disposed on the proximal end of the shaft 58 within the cavity 52. In this manner, the distal end 60 can be threadingly engaged with the threaded bore 402*c*, assuming the distal end 60 is threaded.

In operation, the distal end of shaft 58 is inserted into the anchor 430 such that the threaded bore 402*c* is registered with the threaded end 60. The anchor members 406 of the anchor 430 are registered to slide over opposite surfaces of the posterior portion 410 of the cage when actuation of the anchor drive 54 translates the elongated shaft 58 and thus the distal end 60 in a direction away from the handle 12. As such, the anchor drive 54 drives the heads 406 over the respective surfaces of the anterior portion 410 and into the vertebrae bone V as shown in FIGS. 5 and 6.

Figure 1:
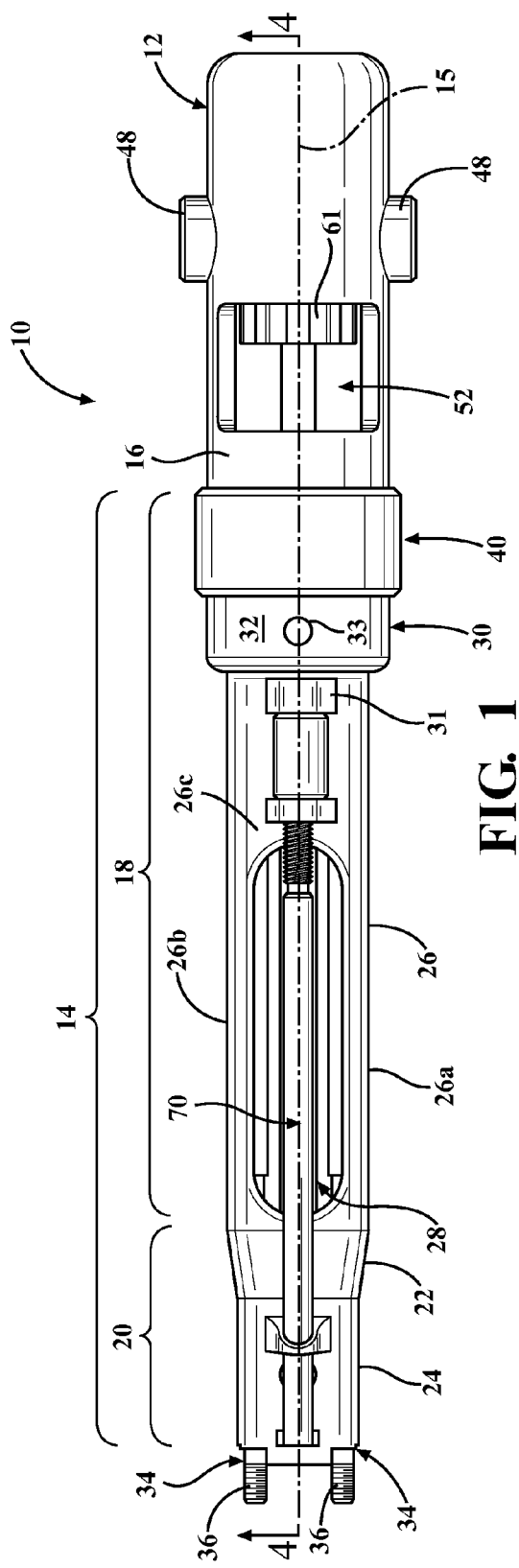
FIG. 1 is a top view of an illustrative embodiment of an instrument disclosed herein.
Figure 2:
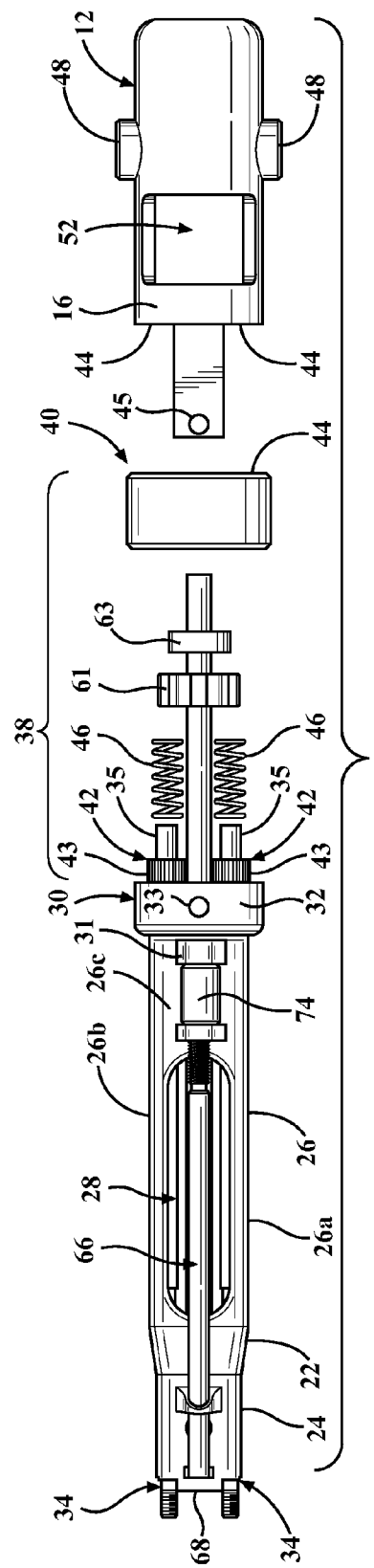
FIG. 2 is a partially exploded view of the instrument shown in FIG. 1.
Figure 3:
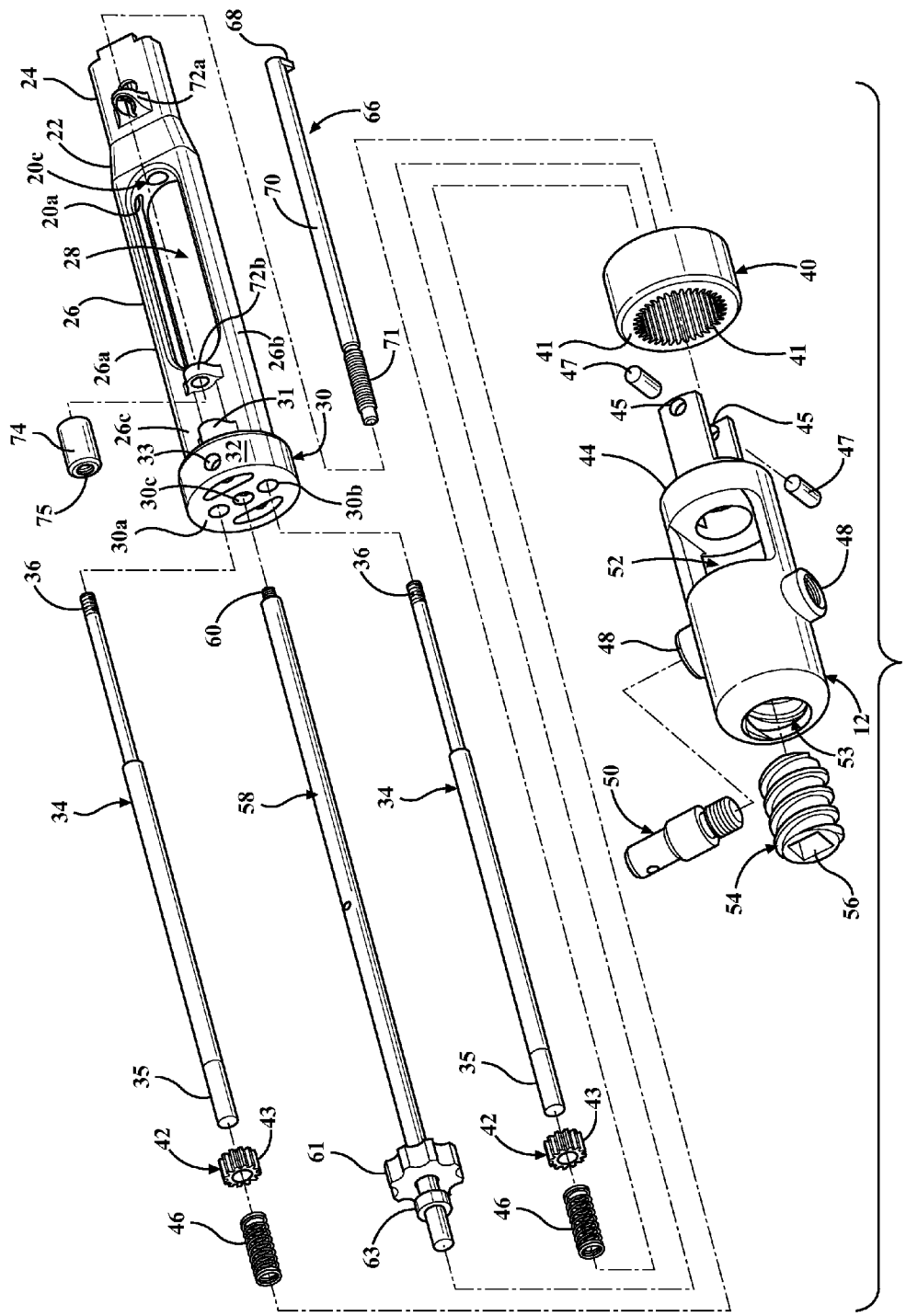
FIG. 3 is a perspective and exploded view of the instrument shown in FIG. 2.
Figure 4:
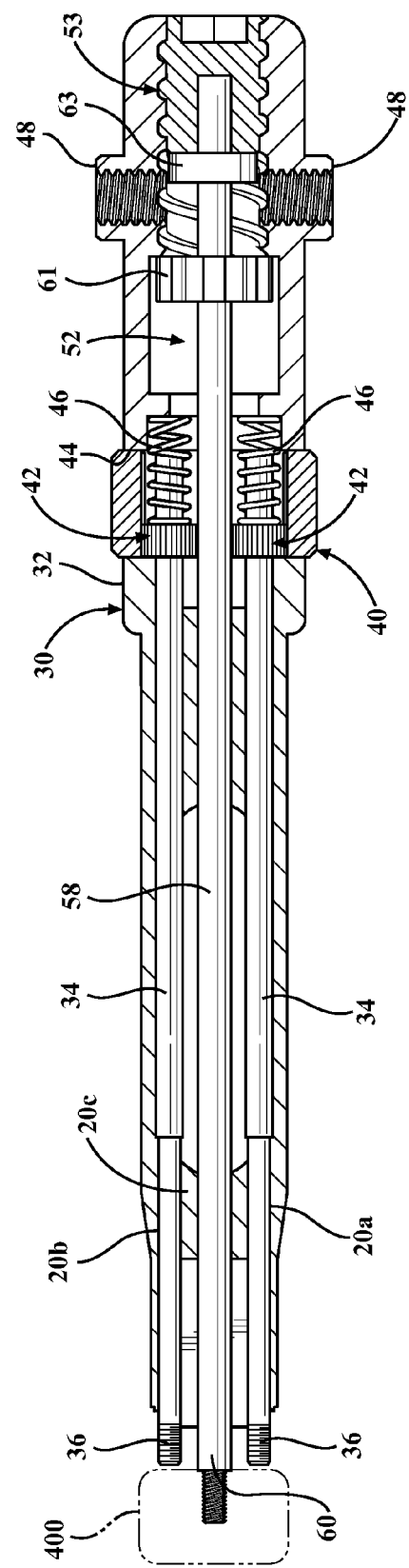
FIG. 4 is a cross sectional view of the instrument shown in FIG. 1 taken along 4-4.

The instrument may further include a stop 66 with a preferred embodiment of the stop 66 provided in FIGS. 1, 2 and 4. The stop 66 is adjustable with respect to the axial length of the instrument 10. The stop 66 includes a planar surface 68 disposed on a distal end of a stop shaft 70. A proximal end 71 of the stop shaft 70 adjacent the handle 12 is threaded. The stop shaft 70 is secured to an outer surface of the housing 14 by a pair of retaining rings 72*a*, 72*b*. The proximal end 71 of the stop shaft 70 is coupled to a stop collar 74 and the stop collar 74 has a threaded inner surface 75 engaged with the threaded outer surface of the proximal end 71. Furthermore, a proximal end of the stop collar 74 abuts against a collar stop 31 and a distal end of the stop collar 74 abuts against the retaining ring 72*b*. Thus, it should be appreciated that rotation of the stop collar 74 will cause an axial displacement of the stop shaft 70, which in turn will adjust the position of the planar surface 68 with respect to the distal end of the housing 14. Accordingly, the user may set a desired depth for which the implant device 400 is implanted by rotating the stop collar 74.

Obviously, many modifications and variations of the present invention are possible in light of the above teachings and may be practiced otherwise than as specifically described while within the scope of the appended claims. As such, the scope of the invention is defined by the claims and all equivalents thereof.

The invention claimed is:

1. An instrument for attachment and insertion of an implant device, the implant device having a pair of threaded bores, an anchor and a drive for deploying the anchor, the anchor deployable so as to fix the implant device within a body, the instrument comprising:
   a handle dimensioned to be gripped;
   a pair of retaining posts each extending longitudinally from a distal end of the handle, each of the pair of retaining posts having a threaded end dimensioned to engage a respective threaded bore of the pair of threaded bores of the implant device and each retaining post having a planetary gear opposite a respective threaded end;
   a post drive mounted to the handle, the post drive being a cylindrical member having an inner circumferential surface with a plurality of gear teeth, the inner circumferential surface engaged with each of the planetary gears of each retaining post and rotation of the post drive rotates each of the retaining posts simultaneously so as to be mechanically connected to each of the pair of retaining posts so as to engage the pair of retaining posts simultaneously, the pair of retaining posts engaging each of the pair of threaded bores of the implant device simultaneously; and
   an anchor drive in mechanical contact with an elongated shaft, the elongated shaft extending longitudinally through a cavity in the handle and having a distal end configured to engage the anchor of the implant device.

2. The instrument as set forth in claim 1, further including a housing, the pair of retaining posts disposed within the housing.

3. The instrument as set forth in claim 2, wherein each of the retaining posts are slidingly and rotatably disposed within a respective bore within the housing.

4. The instrument as set forth in claim 3, wherein each of the retaining posts have a biasing member biasing the retaining posts in a direction towards the implant device.

5. The instrument as set forth in claim 1, wherein the handle of the instrument has a threaded bore and the anchor drive has a complimentary threaded outer surface with rotation of the anchor drive within the threaded bore operable to move the distal end of the elongated shaft in a direction away from the handle and towards the implant device.

6. The instrument as set forth in claim 5, further including a housing, the elongated shaft slidingly and rotatably disposed within a bore within the housing.

7. The instrument as set forth in claim 1, further including a stop disposed proximate a distal end of the pair of retaining posts, the stop configured to prevent the implant device from being inserted into a body past a predetermined depth.

8. The instrument as set forth in claim 7, further including a housing, the stop mounted to an outer surface of the housing.

9. The instrument as set forth in claim 8, wherein the stop is a tubular member having a distal end with a planar surface.

10. The instrument as set forth in claim 9, wherein the stop has a stop collar configured to axially displace the distal end and adjust the maximum depth the implant device is inserted within the body.

11. The instrument as set forth in claim 1, wherein the handle has a threaded opening configured to hold stem of an additional handle, the additional handle configured to assist in holding the handle steady during rotation of the post drive.

12. The medical implant system of claim 1, wherein the instrument further includes a collar, the collar having a pair of bores, each of the pair of retaining posts slidably and rotatably disposed within a respective one of the pair of bores.

13. A medical implant system comprising:
an implant device, the implant device having a pair of threaded bores, an anchor and a drive for deploying the anchor, the anchor deployable so as to fix the implant device within a body;
an instrument for attachment and insertion of the implant device, the instrument having:
a handle dimensioned to be gripped;
a pair of retaining posts each extending longitudinally from a distal end of the handle, each of the pair of retaining posts having an end dimensioned to engage a respective threaded bore of the pair of threaded bores of the implant device and each retaining post having a planetary gear opposite a respective threaded end;
a post drive mounted to the handle, the post drive being a cylindrical member having an inner circumferential surface with a plurality of gear teeth, the inner circumferential surface engaged with each of the planetary gears of each retaining post and rotation of the post drive rotates each of the retaining posts simultaneously so as to be mechanically connected to each of the pair of retaining posts so as to engage the pair of retaining posts simultaneously, the pair of retaining posts engaging each of the pair of threaded bores of the implant device simultaneously and attaching the instrument to the implant device; and
an anchor drive in mechanical contact with an elongated shaft, the elongated shaft extending longitudinally through a cavity in the handle and having a distal end configured to engage the anchor of the implant device.

14. The medical implant system of claim 13, wherein each of the retaining posts have a biasing member biasing the retaining posts in a direction towards the implant device.

15. The medical implant system of claim 14, wherein the handle of the instrument has a threaded bore and the anchor drive has a complimentary threaded outer surface with rotation of the anchor drive within the threaded bore operable to move the distal end of the elongated shaft in a direction away from the handle and towards the implant device.

16. The medical implant system of claim 15, further including a stop disposed proximate a distal end of the pair of retaining posts, the stop configured to prevent the implant device from being inserted into a body past a predetermined depth.

17. The instrument as set forth in claim 13, further including a collar, the collar having a pair of bores, each of the pair of retaining posts slidably and rotatably disposed within a respective one of the pair of bores.

* * * * *